US005614390A

United States Patent [19]
McCaslin et al.

[11] Patent Number: 5,614,390
[45] Date of Patent: Mar. 25, 1997

[54] SPECIES-SPECIFIC DETECTION OF *MYCOBACTERIUM KANSASII*

[75] Inventors: Richard B. McCaslin, Ellicott City; Keith C. Williams, Baltimore, both of Md.

[73] Assignee: Becton, Dickinson and Company, Franklin Lakes, N.J.

[21] Appl. No.: 663,769

[22] Filed: Jun. 14, 1996

[51] Int. Cl.$^6$ ..................................................... C12P 19/34
[52] U.S. Cl. ............................. 435/91.2; 435/6; 536/24.3
[58] Field of Search ........................ 536/24.3; 435/91.2, 435/6

[56] References Cited

U.S. PATENT DOCUMENTS

| 5,352,580 | 10/1994 | Spears et al. | 435/6 |
| 5,500,341 | 3/1996 | Spears | 435/6 |
| 5,518,884 | 5/1996 | Spears et al. | 435/6 |

OTHER PUBLICATIONS

B. C. Ross, et al. "Identification of a Genetically Distinct Subspecies of *Mycobacterium kansasii*" *J. Clin. Microbiol.* 30:2930–2933 (1992).
B. Boddinghaus, et al. "Detection and Identification of Mycobacteria by Amplification of RNA" *J. Clin. Microbiol.* 28:1751–1759 (1990).
T. Rogall, et al., "Differentiation of Mycobacterium species by direct sequencing of amplified DNA" *J. Gen. Microbiol.* 136:1915–1920 (1990).
Z. H. Huang, et al. "Identification of *Mycobacterium kansasii* by DNA Hybridization" *J. Clin. Microbiol.* 29:2125–2129 (1991).
E. Tortoli, et al. "Evaluation of a Commercial DNAN Probe Assay for the Identification of *Mycobacterium kansasii*" *Eur. J. Clin. Microbiol. Infect. Dis.* 13:264–267 (1994).
M. Yang, et al. "Isolation of a DNA Probe for Identification of *Mycobacterium kansasii*, including the Genetic Subgroup" *J. Clin. Microbiol.* 31:2769–2772 (1993).

*Primary Examiner*—Kenneth R. Horlick
*Assistant Examiner*—Joyce Tung
*Attorney, Agent, or Firm*—Donna R. Fugit

[57] ABSTRACT

The present invention provides oligonucleotides useful as amplification primers and assay probes for species-specific detection and identification of *Mycobacterium kansasii*. The oligonucleotides of the invention are derived from the p6123 sequence previously reported by Yang, et al. (1993) and amplify a target sequence of both atypical and typical *M. kansasii* strains, allowing detection and identification of a broad range of *M. kansasii* strains. The oligonucleotides may be used after culture as a means for confirming the identity of the cultured organism or they may be used prior to culture or in place of culture for detection and identification of mycobacterial nucleic acids using a variety of amplification methods.

23 Claims, No Drawings

SPECIES-SPECIFIC DETECTION OF *MYCOBACTERIUM KANSASII*

FIELD OF THE INVENTION

The present invention relates to nucleic acid amplification, including detection and/or identification of microorganisms using nucleic acid amplification.

BACKGROUND OF THE INVENTION

The mycobacteria are a genus of bacteria which are acid-fast, non-motile, gram-positive rods. The genus comprises several species which include, but are not limited to, *Mycobacterium africanum, M. avium, M. bovis, M. bovis-BCG, M. chelonae, M. fortuitum, M. gordonae, M. intracellulare, M. kansasii, M. microti, M. scrofulaceum, M. paratuberculosis* and *M. tuberculosis*. Certain of these organisms are the causative agents of disease. For the first time since 1953, cases of mycobacterial infections are increasing in the United States. Of particular concern is tuberculosis, the etiological agent of which is *M. tuberculosis*. Many of these new cases are related to the AIDS epidemic, which provides an immune compromised population which is particularly susceptible to infection by mycobacteria. Other mycobacterial infections are also increasing as a result of the increase in numbers of immune compromised patients. *Mycobacterium avium, Mycobacterium kansasii* and other non-tuberculosis mycobacteria are found as opportunistic pathogens in HIV infected and other immune compromised patients.

Conventional diagnosis of mycobacterial infections relies on acid-fast staining and cultivation of the organism, followed by biochemical assays. These procedures are time-consuming, and a typical diagnosis using conventional culture methods can take as long as six weeks. Automated culturing systems such as the BACTEC™ system (Becton Dickinson Microbiology Systems, Sparks, Md.) can decrease the time for diagnosis to one to two weeks. However, there is still a need to reduce the time required for diagnosing mycobacterial infections to less than a week, preferably to about one day. Oligonucleotide probe based assays such as Southern hybridizations or dot blots are capable of returning a rapid result (i.e., in one day or less). Assays based on amplification of nucleic acids are usually more sensitive and may provide even more rapid results, often within hours. For diagnosis of mycobacterial infections such methods require development of oligonucleotide probes or primers which are specific for the genus Mycobacterium or specific for a particular species of mycobacteria if specific identification of the organism is desired.

Conventional laboratory identification of *Mycobacterium kansasii* is based upon biochemical testing and determination of growth characteristics. These include catalase production, urease activity, TWEEN hydrolysis, nitrate reduction and the ability of the bacterium to produce pigment when exposed to light (photochromogenicity). Because several other mycobacterial species exhibit a similar biochemical profile, photochromogenicity is generally relied upon for conclusive identification of *Mycobacterium kansasii*. However, determination of photochromogenicity requires a pure culture of the organism and this phenotype can be variable, subjective and difficult to determine reliably. For these reasons, there have been attempts to identify *Mycobacterium kansasii* by species-specific hybridization or nucleic acid amplification using oligonucleotide probes. Z. H. Huang, et al. (1991. *J. Clin. Microbiol.* 29, 2125–2129) have reported a DNA probe obtained from a genomic library with a degree of species-specificity for *Mycobacterium kansasii*. This clone (pMK 1–9) showed some cross-hybridization with other species, including *M. gastri*, and did not detect a genetically distinct subgroup of *M. kansasii*. The nucleotide sequence of pMK1–9 was not reported, nor was the gene from which it may have been derived identified. B. C. Ross, et al. (1992. *J. Clin. Microbiol.* 30, 2930–2933) also reported identification of genetically distinct subspecies of *M. kansasii* using the pMK1–9 probe, a 65 kDa antigen gene probe and a commercial DNA probe test employing probes which specifically hybridize to rRNA (ACCU-PROBE, Gen-Probe, San Diego, Calif.). T. Rogall, et al. (1990. *J. Gen. Microbiol.* 136, 1915–1920) used the 16S rRNA sequence in a polymerase chain reaction (PCR) based sequencing strategy for identification of mycobacterial species. However, these primers could not be used to differentiate *M. gastri* from *M. kansasii* because the 16S rRNA sequence from these two species is identical in spite of their differing phenotypic characteristics. Similar studies have been published by B. B öddinghaus, et al. (1990. *J. Clin. Microbiol.* 28, 1751–1759), who reported oligonucleotides derived from 16S rRNA sequences which are specific for the *M. tuberculosis* group, i.e., *M. avium-M. paratuberculosis*, and *M. intracellulare*. M. Yang, et al. (1993. *J. Clin. Microbiol.* 31, 2769–2772) have reported isolation of a sequence from a clinical isolate which, when used as a hybridization probe, exhibits *M. kansasii* species-specificity. This probe (p6123) hybridized to all *M. kansasii* strains tested, including the subgroup which is pMK1–9 negative. P. A. Spears (U.S. Pat. No. 5,500,341) describes *M. kansasii*-specific primers derived from the region of p6123 between nucleotides 51 and 220.

The following terms are defined herein as follows:

An amplification primer is a primer for amplification of a target sequence by extension of the primer after hybridization to the target sequence. Amplification primers are typically about 10–75 nucleotides in length, preferably about 15–50 nucleotides in length. The total length of an amplification primer for SDA is typically about 25–50 nucleotides. The 3' end of an SDA amplification primer (the target binding sequence) hybridizes at the 3' end of the target sequence. The target binding sequence is about 10–25 nucleotides in length and confers hybridization specificity on the amplification primer. The SDA amplification primer further comprises a recognition site for a restriction endonuclease 5' to the target binding sequence. The recognition site is for a restriction endonuclease which will nick one strand of a DNA duplex when the recognition site is hemimodified, as described by G. Walker, et al. (1992. *PNAS* 89:392–396 and 1992 *Nucl. Acids Res.* 20:1691–1696). The nucleotides 5' to the restriction endonuclease recognition site (the "tail") function as a polymerase repriming site when the remainder of the amplification primer is nicked and displaced during SDA. The repriming function of the tail nucleotides sustains the SDA reaction and allows synthesis of multiple amplicons from a single target molecule. The tail is typically about 10–25 nucleotides in length. Its length and sequence are generally not critical and can be routinely selected and modified to obtain the desired $T_m$ for hybridization. As the target binding sequence is the portion of a primer which determines its target-specificity, for amplification methods which do not require specialized sequences at the ends of the target the amplification primer generally consists essentially of only the target binding sequence. For amplification methods which require specialized sequences appended to the target other than the nickable restriction endonuclease recognition site and the tail of SDA (e.g., an RNA polymerase promoter for 3SR, NASBA or transcription based amplification), the required specialized sequence may be linked to the target binding sequence using routine methods for preparation of oligonucletoides without altering the hybridization specificity of the primer.

A bumper primer or external primer is a primer used to displace primer extension products in isothermal amplification reactions. The bumper primer anneals to a target sequence upstream of the amplification primer such that extension of the bumper primer displaces the downstream amplification primer and its extension product.

The terms target or target sequence refer to nucleic acid sequences to be amplified. These include the original nucleic acid sequence to be amplified, the complementary second strand of the original nucleic acid sequence to be amplified and either strand of a copy of the original sequence which is produced by the amplification reaction. These copies serve as amplifiable targets by virtue of the fact that they contain copies of the sequence to which the amplification primers hybridize.

Copies of the target sequence which are generated during the amplification reaction are referred to as amplification products, amplimers or amplicons.

The term extension product refers to the copy of a target sequence produced by hybridization of a primer and extension of the primer by polymerase using the target sequence as a template.

The term species-specific refers to detection, amplification or oligonucleotide hybridization in a species of organism or a group of related species without substantial detection, amplification or oligonucleotide hybridization in other species of the same genus or species of a different genus.

The term assay probe refers to any oligonucleotide used to facilitate detection or identification of a nucleic acid. For example, in the present invention, assay probes are used for detection or identification of *Mycobacterium kansasii* nucleic acids. Detector probes, detector primers, capture probes and signal primers as described below are examples of assay probes.

SUMMARY OF THE INVENTION

The present invention provides oligonucleotides useful as amplification primers and assay probes for species-specific detection and identification of *Mycobacterium kansasii*. Species-specificity means that the inventive primers amplify a target sequence in *M. kansasii* nucleic acids with little or no detectable amplification of target sequences of other species of mycobacteria or of closely related microorganisms such as *M. gastri*, *Rhodococcus rhodochrous* and *Nocardia asteroides*. The amplification primers of the invention are derived from the p6123 sequence previously reported by Yang, et al. (1993). The primers of the invention are derived from a different region of p6123 than those of U.S. Pat. No. 5,500,341, as the target described in the '341 patent contains a BsoBI site which makes it unsuitable for tSDA when BsoBI is the selected nickable restriction endonuclease site. The primers of the invention amplify the target sequence in both atypical and typical *M. kansasii* strains, allowing sensitive detection and identification of a broad range of *M. kansasii* strains. Optimization of the primers for use in tSDA permits increased amplification efficiency in shorter reaction times.

The oligonucleotides of the invention may be used after culture as a means for confirming the identity of the cultured organism. Alternatively, they may be used prior to culture or in place of culture for detection and identification of mycobacterial nucleic acids using known amplification methods. In either case, the inventive oligonucleotides and assay methods provide a means for rapidly discriminating between the nucleic acids of *M. kansasii* and other species of mycobacteria, allowing the practitioner to rapidly identify this microorganism without resorting to the time-consuming phenotypic and biochemical procedures customarily relied upon. Such rapid identification of the specific etiological agent involved in a mycobacterial infection provides information which can be used to determine appropriate therapy within a short period of time.

DETAILED DESCRIPTION OF THE INVENTION

The present invention provides oligonucleotides, amplification primers and assay probes which exhibit *M. kansasii*-specificity in nucleic acid amplification reactions. Also provided are methods for detecting and identifying *M. kansasii* nucleic acids using the oligonucleotides of the invention. All of the *M. kansasii* isolates tested (both typical and atypical strains) were positive in amplification assays using the inventive oligonucleotides.

Primers MY-4 (TCGCAGAACGCGACAAACGGTG, SEQ ID NO: 1) and MY-1 (TGATGAAACGTGTTTTGC-CAGCG, SEQ ID NO: 2) were designed based on the p6123 sequence published by Yang, et al. and used in a PCR reaction to amplify a 331 base pair segment of the 500 base pair fragment contained in the p6123 clone. This segment was amplified and sequenced in thirteen typical and atypical isolates of *M. kansasii*. The sequences obtained were aligned in an attempt to design amplification primers which would species-specifically amplify a target in both typical and atypical strains of *M. kansasii*. Target binding sequences for four sets of amplification primers were selected based on the sequence alignments. The four primer sets defined overlapping target sequences within the 331 base pair segment. Primers comprising the target binding sequences and the additional sequences required for SDA were synthesized and tested. Surprisingly, only one of the sets resulted in efficient amplification of the p6123 target in this region. The remaining three sets either did not amplify the target at any detectable level or were too insensitive to be useful in diagnostic applications. Optimization of the amplification reaction conditions failed to improve amplification efficiency using these three primer sets. The primer set which provided efficient amplification consisted of target binding sequences for three upstream amplification primers and two downstream amplification primers, as shown in Table 1. In Table 1, the target binding sequences are italicized and the exemplary restriction site (BsoBI) is bolded.

TABLE 1

Upstream amplification primers for SDA:

SEQ ID NO:3 (6123ALT1)
5'CGATTCCGCTCCAGACTTCTCGGG*ACGACGATTGGGCA*3'

SEQ ID NO:4 (6123ALT2)
5'CGATTCCGCTCCAGACTTCTCGGG*CACGACGATTGGGC*3'

SEQ ID NO:5 (6123AL46)
5'CGATTCCGCTCCAGACTTCTCGGG*ACGACGATCGGGCA*3'

TABLE 1-continued

Downstream amplification primers for SDA:

SEQ ID NO:6 (6123AR44)
5'ACCGCATCGAATGCATGTCTCGGGGCCGACGAGCTGT3'

SEQ ID NO:7 (6123AR48)
5'ACCGCATCGAATGCATGTCTCGGGGCCGACGAGCTGTG3'

For testing amplification efficiency and specificity in SDA, the bumper primers required for SDA and assay probes for use in detecting amplification products were also designed based on the sequence alignments. These included bumper primer B 1 (5'AGTGGTCATGAGATG3', SEQ ID NO: 8), bumper primer B2 (5'CGGACTTCTTTCGT3', SEQ ID NO: 9), and three detector probes (D1A, 5'CTGCTGGACACCAC3', SEQ ID NO: 10; D2A, 5'AGCCGTTCCAGGAC3', SEQ ID NO: 11; D3A, 5'GCCGGTGGTGTCCA3', SEQ ID NO: 12).

As nucleic acids do not require complete complementarity in order to hybridize, it is to be understood that the probe and primer sequences herein disclosed may be modified to some extent without loss of utility as *M. kansasii*-specific probes and primers. As is known in the art, hybridization of complementary and partially complementary nucleic acid sequences may be obtained by adjustment of the hybridization conditions to increase or decrease stringency (i.e., adjustment of hybridization temperature or salt content of the buffer). Such minor modifications of the disclosed sequences and any necessary adjustments of hybridization conditions to maintain *M. kansasii*-specificity require only routine experimentation and are within the ordinary skill in the art.

The amplification products generated using the inventive primers may be detected by a characteristic size, for example on polyacrylamide or agarose gels stained with ethidium bromide. Alternatively, amplified *M. kansasii* target sequences may be detected by means of an assay probe, which is an oligonucleotide tagged with a detectable label. In one embodiment, at least one tagged assay probe may be used for detection of amplified target sequences by hybridization (a detector probe), by hybridization and extension as described by Walker, et al., *Nucl. Acids Res.*, supra (a detector primer) or by hybridization, extension and conversion to double stranded form as described in EP 0 678 582 (a signal primer). Preferably, the assay probe is selected to hybridize to a sequence in the target which is between the amplification primers, i.e., it should be an internal assay probe. Alternatively, an amplificatioin primer or the target binding sequence thereof may be used as the assay probe.

The detectable label of the assay probe is a moiety which can be detected either directly or indirectly as an indication of the presence of the target nucleic acid. For direct detection of the label, assay probes may be tagged with a radioisotope and detected by autoradiography or tagged with a fluorescent moiety and detected by fluorescence as is known in the art. Alternatively, the assay probes may be indirectly detected by tagging with a label which requires additional reagents to render it detectable. Indirectly detectable labels include, for example, chemiluminescent agents, enzymes which produce visible reaction products and ligands (e.g., haptens, antibodies or antigens) which may be detected by binding to labeled specific binding partners (e.g., antibodies or antigens/haptens). Ligands are also useful immobilizing the ligand-labeled oligonucleotide (the capture probe) on a solid phase to facilitate its detection. Particularly useful labels include biotin (detectable by binding to labeled avidin or streptavidin) and enzymes such as horseradish peroxidase or alkaline phosphatase (detectable by addition of enzyme substrates to produce colored reaction products). Methods for adding such labels to, or including such labels in, oligonucleotides are well known in the art and any of these methods are suitable for use in the present invention.

Examples of specific detection methods which may be employed include a chemiluminescent method in which amplified products are detected using a biotinylated capture probe and an enzyme-conjugated detector probe as described in U.S. Pat. No. 5,470,723. After hybridization of these two assay probes to different sites in the assay region of the target sequence (between the binding sites of the two amplification primers), the complex is captured on a streptavidin-coated microtiter plate by means of the capture probe, and the chemiluminescent signal is developed and read in a luminometer. As another alternative for detection of amplification products, a signal primer as described in EP 0 678 582 may be included in the SDA reaction. In this embodiment, labeled secondary amplification products are generated during SDA in a target amplification-dependent manner and may be detected as an indication of target amplification by means of the associated label.

For commercial convenience, amplification primers for species-specific detection and identification of *M. kansasii* nucleic acids may be packaged in the form of a kit. Typically, such a kit contains at least one pair of amplification primers according to the present invention. Reagents for performing a nucleic acid amplification reaction may also be included with the *M. kansasii*-specific amplification primers, for example, buffers, additional primers, nucleotide triphosphates, enzymes, etc. The components of the kit are packaged together in a common container, optionally including instructions for performing a specific embodiment of the inventive methods. Other optional components may also be included in the kit, e.g., an oligonucleotide tagged with a label suitable for use as an assay probe, and/or reagents or means for detecting the label.

The target binding sequences of the amplification primers confer species hybridization specificity on the oligonucleotides and therefore provide species-specificity to the amplification reaction. Other sequences, as required for performance of a selected amplification reaction, may optionally be added to the target binding sequences disclosed herein without altering the species-specificity of the oligonucleotide. By way of example, the *M. kansasii*-specific amplification primers of the invention may contain a recognition site for the restriction endonuclease BsoBI which is nicked during the SDA reaction. It will be apparent to one skilled in the art that other nickable restriction endonuclease recognition sites may be substituted for the BsoBI recognition site, including but not limited to those recognition sites disclosed in EP 0 684 3 15. Preferably, the recognition site is for a thermophilic restriction endonuclease so that the amplification reaction may be performed under the conditions of thermophilic SDA (tSDA). Similarly, the tail sequence of the amplification primer (5' to the restriction endonuclease recognition site) is generally not critical, although the restriction site used for SDA and sequences which will hybridize either to their own target binding sequence or to the other primers should be avoided. Amplification primers for SDA according to the invention therefore consist of the 3' target binding sequences indicated in Table I, a nickable restriction endonuclease recognition site 5' to the target binding sequence and a tail sequence about 10–25 nucleotides in length 5' to the restriction endonuclease recognition site. The nickable restriction endonuclease recognition site and the tail sequence are sequences required for the SDA reaction. For other amplification reactions, the amplification primers according to the invention may consist of the disclosed target binding sequences only (e.g., for PCR) or the target binding sequence and additional sequences required for the selected amplification reaction (e.g., sequences required for SDA as described above or a promoter recognized by RNA polymerase for 3 SR).

In SDA, the bumper primers are not essential fir species-specificity, as they function to displace the downstream, species-specific amplification primers. It is only required that the bumper primers hybridize to the target upstream from the amplification primers so that when they are extended they will displace the amplification primer and its extension product. The particular sequence of the bumper primer is therefore generally not critical, and may be derived from any upstream target sequence which is sufficiently close to the binding site of the amplification primer to allow displacement of the amplification primer extension product upon extension of the bumper primer. Occasional mismatches with the target in the bumper primer sequence or some cross-hybridization with non-target sequences do not generally negatively affect amplification efficiency as long as the bumper primer remains capable of hybridizing to the specific target sequence. However, the bumper primers described herein are species-specific for *M. kansasii* and may therefore also be used as target binding sequences in amplification primers, if desired.

Amplification reactions employing the primers of the invention may incorporate thymine as taught by Walker, et al., supra, or they may wholly or partially substitute 2'-deoxyuridine 5'-triphosphate for TTP in the reaction to reduce cross-contamination of subsequent amplification reactions, e.g., as taught in EP 0 624 643. dU (uridine) is incorporated into amplification products and can be excised by treatment with uracil DNA glycosylase (UDG). These abasic sites render the amplification product unamplifiable in subsequent amplification reactions. UDG may be inactivated by uracil DNA glycosylase inhibitor (Ugi) prior to performing the subsequent amplification to prevent excision of dU in newly-formed amplification products.

EXAMPLE 1

The amplification primers described in Table 1 were evaluated in tSDA in all upstream/downstream pairwise combinations to determine their ability to amplify the target in *M. kansasii*. Four different amplification reaction conditions were tested to optimize the reaction, as shown in Table 2:

TABLE 2

| $KPO_4$ (mM) | Temperature (°C.) | DMSO (%) |
|---|---|---|
| 25 | 50 | 15 |
| 25 | 52 | 10 |
| 35 | 50 | 10 |
| 35 | 52 | 15 |

Thermophilic SDA was performed essentially as described in EP 0 684 315 and amplification products were detected by hybridization and extension of a $^{32}P$-labeled primer as described by Walker, et al., *Nucl. Acids Res.*, supra. Each amplification reaction contained $10^6$ *M. kansasii* genomes (TMC 1201), 550 ng human DNA, 6.5 mM magnesium acetate, 5.15% glycerol, 160 units BsoBI, 12.5 units Bst polymerase, 0.5 μM amplification primers and 0.05 μM bumper primers. SEQ ID NO: 11 was the assay probe selected for hybridization and extension. Amplification was allowed to proceed at the indicated temperatures for 30 min.

All combinations of upstream and downstream amplification primers in this set detectably amplified the target under all reaction conditions. The optimum amplification efficiency was obtained in 10% DMSO, 35 mM $KPO_4$ at 50° C.

EXAMPLE 2

The specificity and crossreactivity of the SEQ ID NO: 5/SEQ ID NO: 6 amplification primer pair were evaluated in amplification reactions employing typical and atypical strains of *M. kansasii*, other species of mycobacteria and non-mycobacterial species. The amplification reactions were performed using the optimized reaction conditions established in Example 1 (35 mM $KPO_4$, 10% DMSO, 50° C.). For cross-reactivity studies, $10^7$ genomes of each of five non-*M. kansasii* species of mycobacteria (*M. gastri* ATCC 1301, *M. gordonae* ATCC 1318, *M. marinarum* ATCC 801, *M. terrae* ATCC 3010 and *M. tuberculosis* ATCC H37Rv) were mixed for use in a single amplification reaction. Similarly, $10^7$ genome copies of each of five non-mycobacterial species (*Actinomyces israelii* ATCC 10049, *Corynebacterium diphtheriae* ATCC 11913, *Nocardia asteroides* ATCC 3308, *Rhodococcus rhodochrous* ATCC 13808 and *Streptomyces somaliens* ATCC 13201) were mixed for amplification. To detect amplification inhibition in the cross-reactivity reactions, the genome mixtures were spiked with $2\times10^4$ genome copies of the *M. kansasii* target (TMC 1201) and amplified in parallel as positive controls. SEQ ID NO: 10 was used as a detector primer to detect amplification in all samples and SEQ ID NO: 11 was used as a detector primer to detect amplification in seven of the samples.

Target amplification was successfully detected in all of the *M. kansasii* strains tested, including both typical strains (ATCC 12478, TMC 1201, LCDC 711, LCDC 714, LCDC 715) and atypical strains (T-1689, T-1492, T-8594, T-10892). Amplification of the p6123 target was also detected in a strain which had not been conclusively identified as either atypical or typical (LCDC 707). At low target concentrations a difference in sensitivity between the two detector primers was sometimes observed, with SEQ ID NO: 11 providing improved sensitivity in some assays. Using SEQ ID NO: 10 as the detector primer, no amplification was detected in the pooled non-*M. kansasii* mycobacterial targets except when the TMC 1201 target was also present. The SEQ ID NO: 11 detector primer produced a band of atypical size in the non-*M. kansasii* mycobacterial targets which could be distinguished from a true positive amplification reaction. Similarly, the SEQ ID NO: 10 detector primer detected no amplification in the pooled non-mycobacterial targets except when the TMC 1201 target was present, but SEQ ID NO: 11 produced a minor nonspecific band. It was therefore concluded that, although both sense assay probes (SEQ ID NO: 11 and SEQ ID NO: 12) and antisense assay probes (SEQ ID NO: 10) are useful in the invention, the anti-sense assay probes produce a cleaner result. These experiments establish that the amplification primers of the invention are species-specific for *M. kansasii* and are capable of amplifying both atypical and typical strains.

EXAMPLE 3

The sensitivity of p6123 target detection in typical strains of *M. kansasii* was determined by titrating the initial genome copy number present in the amplification reaction. Genomic DNA was isolated from strain TMC 1201 and diluted in 50 ng of human placental DNA. SDA reactions (50 μl) were performed using $10^6$, $10^5$, $10^4$, $10^3$, $10^2$ and 10 TMC 1201 genomes as the starting target number. Amplification was performed essentially as described in the previous examples (35 mM $KPO_4$, 100 μg/ml acetylated bovine serum albumin, 1.4 mM thio-dCTP, 0.5 mM dUTP, 0.2 mM dGTP, 0.2 mM dATP, 10% DMSO, 6.5 mM magnesium acetate, 0.5 μM amplification primers, 0.05 μM bumper primers, 550 ng human placental DNA, 12.5 units Bst polymerase, 160 units BsoBI, 1 unit uracil-N-glycosylase, 2 units uracil-N-glycosylase inhibitor, 50° C. for 30 min.), pairing each of the three upstream primers with SEQ ID NO: 6 and using SEQ ID NO: 8 and SEQ ID NO: 9 as the bumper primers. Amplification products were detected by hybridization and extension of a $^{32}$P-labeled detector primer (either SEQ ID NO: 10 or SEQ ID NO: 11) as before. The lowest initial target copy number tested (10 genomes) was readily detected with either the sense or antisense detector probe, indicating that the sensitivity of the assay is 10 genomes or less. In typical strains, selection of the assay probe (sense or antisense) does not appear to affect the sensitivity of the assay.

The sensitivity of p6123 target detection in atypical strains of *M. kansasii* was determined in a similar manner, using T-10892 genomic DNA as the atypical target. The minimum initial target copy number detectable after amplification using the sense detector primer SEQ ID NO: 12 was about $10^4$ genomes. Similar results were obtained using the complement of SEQ ID NO: 10 (sense) as the detector primer.

SEQ ID NOs: 10–12 and the complements thereof are all useful as assay probes in the invention. However; in general it was noted that sense assay probes produced minor but detectable levels of background and provided greater sensitivity in the assay than antisense assay probes. SEQ ID NO: 12 was an exception, producing a clean assay result (essentially no background) and higher sensitivity. Reduced background was generally observed in assays using antisense assay probes, but sensitivity was also typically somewhat reduced. It is possible that the differences in sensitivity between sense and antisense assay probes is the result of asymmetrical amplification of the two complementary target strands.

What is claimed is:

1. An oligonucleotide consisting of a target binding sequence selected from the group consisting of the target binding sequences of SEQ ID NO: 3, SEQ ID NO: 4, SEQ ID NO: 5, SEQ ID NO: 6 and SEQ ID NO: 7 and, optionally, a sequence required for an amplification reaction.

2. The oligonucleotide of claim 1 wherein the sequence required for the amplification reaction comprises a restriction endonuclease recognition site which is nicked by a restriction endonuclease in the amplification reaction.

3. The oligonucleotide of claim 2 selected from the group consisting of SEQ ID NO: 3, SEQ ID NO: 4, SEQ ID NO: 5, SEQ ID NO: 6 and SEQ ID NO: 7.

4. An oligonucleotide selected from the group consisting of SEQ ID NO: 8, SEQ ID NO: 9, SEQ ID NO: 10, SEQ ID NO: 11, SEQ ID NO: 12 and complements thereof.

5. A method for amplifying a target nucleic acid of *Mycobacterium kansasii* comprising:
   a) hybridizing to the target nucleic acid
      i) a first amplification primer consisting of a target binding sequence selected from the group consisting of the target binding sequences of SEQ ID NO: 3, SEQ ID NO: 4 and SEQ ID NO: 5 and, optionally, a sequence required for an amplification reaction, and
      ii) a second amplification primer consisting of a target binding sequence selected from the group consisting of the target binding sequences of SEQ ID NO: 6 and SEQ ID NO: 7 and, optionally, the sequence required for the amplification reaction, and;
   b) amplifying the target nucleic acid by extending the hybridized first and second amplification primers.

6. The method of claim 5 further comprising detecting the amplified target nucleic acid by means of an assay probe.

7. The method of claim 6 wherein the assay probe consists of SEQ ID NO: 10, SEQ ID NO: 11, SEQ ID NO: 12 or a complement thereof tagged with a detectable label.

8. The method of claim 6 wherein the assay probe consists of the target binding sequence of SEQ ID NO: 3, the target binding sequence of SEQ ID NO: 4, the target binding sequence of SEQ ID NO: 5, the target binding sequence of SEQ ID NO: 6 or the target binding sequence of SEQ ID NO: 7 tagged with a detectable label.

9. The method of claim 5 wherein the sequence required for the amplification reaction comprises a recognition site for a restriction endonuclease which is nicked by the restriction endonuclease during amplification.

10. The method of claim 9 wherein the first amplification primer consists of SEQ ID NO: 3, SEQ ID NO: 4 or SEQ ID NO: 5 and the second amplification primer consists of SEQ ID NO: 6 or SEQ ID NO: 7.

11. The method of claim 10 wherein the hybridized first and second amplification primers are displaced from the target nucleic acid by extension of a first bumper primer consisting of SEQ ID NO: 8 and a second bumper primer consisting of SEQ ID NO: 9.

12. The method of claim 5 wherein the target nucleic acid is amplified by the Polymerase Chain Reaction.

13. The method of claim 5 wherein the target nucleic acid is amplified by Strand Displacement Amplification.

14. The method of claim 5 wherein the target nucleic acid is amplified by 3SR.

15. A method for amplifying a target nucleic acid of *Mycobacterium kansasii* comprising:
   a) hybridizing to the target nucleic acid
      i) a first amplification primer consisting of SEQ ID NO: 3, SEQ ID NO: 4 or SEQ ID NO: 5, and
      ii) a second amplification primer consisting of SEQ ID NO: 6 or SEQ ID NO: 7, and;
   b) amplifying the target nucleic acid in a Strand Displacement Amplification reaction.

16. The method of claim 15 further comprising detecting the amplified target nucleic acid by means of an assay prob 17. The method of claim 16 wherein the assay probe consists of SEQ ID NO: 10, SEQ ID NO: 11, SEQ ID NO: 12 or a complement thereof tagged with a detectable label.

18. The method of claim 15 wherein the first amplification primer consists of SEQ ID NO: 5 and the second amplification primer consists of SEQ ID NO: 6.

19. The method of claim 18 wherein the hybridized first and second amplification primers are displaced from the target nucleic acid by extension of a first bumper primer consisting of SEQ ID NO: 8 and a second bumper primer consisting of SEQ ID NO: 9.

20. A kit for amplification of a target nucleic acid of *Mycobacterium kansasii* comprising:
  a) a first amplification primer consisting of a target binding sequence selected from the group consisting of the target binding sequences of SEQ ID NO: 3, SEQ ID NO: 4 and SEQ ID NO: 5 and, optionally, a sequence required for an amplification reaction;
  b) a second amplification primer consisting of a target binding sequence selected from the group consisting of the target binding sequences of SEQ ID NO: 6 and SEQ ID NO: 7 and, optionally, the sequence required for the amplification reaction, and;
  c) a reagent for amplification of the target sequence.

21. The kit of claim 20 further comprising an assay probe.

22. The kit of claim 21 wherein the assay probe is selected from the group consisting of SEQ ID NO: 10, SEQ ID NO: 11, SEQ ID NO: 12 and complements thereof.

23. The kit of claim 20 wherein the reagent for amplification of the target sequence is a reagent for Strand Displacement Amplification.

* * * * *

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

TCGCAGAACG CGACAAACGG TG        22

( 2 ) INFORMATION FOR SEQ ID NO:2:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

TGATGAAACG TGTTTTGCCA GCG        23

( 2 ) INFORMATION FOR SEQ ID NO:3:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

CGATTCCGCT CCAGACTTCT CGGGACGACG ATTGGGCA        38

( 2 ) INFORMATION FOR SEQ ID NO:4:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:4:

```
CGATTCCGCT CCAGACTTCT CGGGCACGAC GATTGGGC                       38
```

( 2 ) INFORMATION FOR SEQ ID NO:5:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

```
CGATTCCGCT CCAGACTTCT CGGGACGACG ATCGGGCA                       38
```

( 2 ) INFORMATION FOR SEQ ID NO:6:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

```
ACCGCATCGA ATGCATGTCT CGGGGCCGAC GAGCTGT                        37
```

( 2 ) INFORMATION FOR SEQ ID NO:7:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

```
ACCGCATCGA ATGCATGTCT CGGGGCCGAC GAGCTGTG                       38
```

( 2 ) INFORMATION FOR SEQ ID NO:8:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

```
AGTGGTCATG AGATG                                                15
```

( 2 ) INFORMATION FOR SEQ ID NO:9:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

```
CGGACTTCTT TCGT                                                 14
```

( 2 ) INFORMATION FOR SEQ ID NO:10:

( i ) SEQUENCE CHARACTERISTICS:
        ( A ) LENGTH: 14 base pairs (B) TYPE: nucleic acid
(C) STRANDEDNESS: single
(D) TOPOLOGY: linear (xi) SEQUENCE DESCRIPTION: SEQ ID NO:10:

CTGCTGGACA CCAC                                                                 14

(2) INFORMATION FOR SEQ ID NO:11:

(i) SEQUENCE CHARACTERISTICS:
(A) LENGTH: 14 base pairs
(B) TYPE: nucleic acid
(C) STRANDEDNESS: single
(D) TOPOLOGY: linear (xi) SEQUENCE DESCRIPTION: SEQ ID NO:11:

AGCCGTTCCA GGAC                                                                 14

(2) INFORMATION FOR SEQ ID NO:12:

(i) SEQUENCE CHARACTERISTICS:
(A) LENGTH: 14 base pairs
(B) TYPE: nucleic acid
(C) STRANDEDNESS: single
(D) TOPOLOGY: linear (xi) SEQUENCE DESCRIPTION: SEQ ID NO:12:

GCCGGTGGTG TCCA                                                                 14